United States Patent [19]

Su et al.

[11] Patent Number: 4,748,189

[45] Date of Patent: May 31, 1988

[54] OPHTHALMIC SOLUTIONS AND METHODS FOR IMPROVING THE COMFORT AND SAFETY OF CONTACT LENSES

[75] Inventors: Kai C. Su, Alpharetta; Lynn Winterton, Roswell, both of Ga.

[73] Assignee: Ciba-Geigy Corporation, Ardsley, N.Y.

[21] Appl. No.: 834,998

[22] Filed: Feb. 27, 1986

Related U.S. Application Data

[63] Continuation-in-part of Ser. No. 726,065, Apr. 15, 1985, abandoned.

[51] Int. Cl.$^4$ ............... A61K 9/12; A61K 47/00; A61K 9/08; A61K 9/10
[52] U.S. Cl. .................... 514/781; 252/106; 252/546; 424/153; 514/772; 514/769; 514/788; 514/839; 514/912; 514/915
[58] Field of Search ............... 514/781, 839, 772, 788, 514/769, 912, 915; 424/153; 252/106, 546

[56] References Cited

U.S. PATENT DOCUMENTS

| | | | |
|---|---|---|---|
| 3,689,673 | 9/1972 | Phares | 424/326 |
| 3,954,644 | 5/1976 | Krezanoski et al. | 252/106 |
| 3,954,965 | 5/1976 | Boghosian et al. | 424/81 |
| 4,029,817 | 6/1977 | Blanco et al. | 424/80 |
| 4,127,423 | 11/1978 | Rankin | 424/127 |
| 4,323,467 | 4/1982 | Fu | 252/106 |
| 4,356,100 | 10/1982 | Sherman | 252/106 |
| 4,409,205 | 10/1983 | Shively | 424/78 |
| 4,438,011 | 3/1984 | Howes | 252/106 |
| 4,510,065 | 4/1985 | Sherman | 252/106 |
| 4,560,491 | 12/1985 | Sherman | 252/106 |
| 4,599,195 | 7/1986 | Schäfer | 252/546 |

FOREIGN PATENT DOCUMENTS

| | | |
|---|---|---|
| 1888 | 6/1979 | European Pat. Off. . |
| 55048 | 6/1982 | European Pat. Off. . |
| 76136 | 4/1983 | European Pat. Off. . |
| 79185 | 5/1983 | European Pat. Off. . |
| 2515201 | 4/1983 | France . |
| 2019600 | 10/1978 | United Kingdom . |

OTHER PUBLICATIONS

Shively et al., "Ophthalmic Drug Delivery Systems", Symposium, Kansas City, Missouri, 1979 (published 1980, Joseph R. Robinson, Ed, American Pharmaceutical Assoc., Publishers) 119–137.
Label from a commercial ophthalmic solution called Clerz.
Reader, Journal of Pharmaceutical Sciences, 73, 840–841 (1984).
Chem Abst 93:192035e (1980)—Ogata.
Handbook of Nonprescription Drugs, 6th ed, 1979, pp. 294–303, Am. Pharm. Assoc.

*Primary Examiner*—Douglas W. Robinson
*Attorney, Agent, or Firm*—Irving M. Fishman

[57] ABSTRACT

An ophthalmic solution for improving the exchange of fluid in the area outside a hydrogel contact lens with the fluid in the area underneath the hydrogel contact lens comprising:
(a) 0.0005% by weight to an amount of a hydrogel contact lens flattening agent equivalent to 330 milliosmoles/kg;
(b) an amount of a viscosity enhancing agent sufficient to cause the composition to have a Brookfield relative viscosity of 3 to 50 cps; and
(c) an amount of an ionic salt sufficient to render the solution substantially isotonic.

The invention also includes a method for improving the exchange of fluid in the area outside a hydrogel contact lens with the fluid in the area underneath the hydrogel contact lens in a human eye comprising adding to said eye an effective amount of such ophthalmic solutions.

46 Claims, No Drawings

OPHTHALMIC SOLUTIONS AND METHODS FOR IMPROVING THE COMFORT AND SAFETY OF CONTACT LENSES

This application is a continuation in part of Ser. No. 06/726,065, filed 04/15/85, now abandoned.

BACKGROUND

1. Field of the Invention

The present invention is directed to ophthalmic solutions for improving the safety and comfort of wearers of contact lenses and to methods for improving the comfort and safety of wearers of such lenses by means of such solutions.

2. Background of the Invention

Contact lenses have provided a useful alternative to eyeglasses for correcting faulty vision. Originally, contact lenses were made of a hard plastic such as methyl methacrylate polymers. More recently, soft contact lenses more comfortable than the hard lenses have become available. Soft contact lenses may be produced by using hydrogels such as those comprising polymers of hydroxyethyl methacrylate.

Hydrogel contact lenses can be arbitrarily divided into those suitable only for daily wear (daily wear lenses) and those suitable for extended wear in addition to daily wear (extended wear lenses). Daily wear lenses are removed every day for cleaning. Extended wear lenses may be worn more than one day before they are removed for cleaning. For example, extended wear lenses may be worn up to about 9 months and even more before removal.

Hydrogel lenses suitable for extended wear generally have higher water contents and/or are thinner than those suitable for daily wear. For example, hydrogel extended wear lenses typically have water contents of at least about 42%, preferably at least about 45% and most preferably at least about 55% by weight and/or a center thickness less than about 0.045 mm, preferably less than about 0.040 mm, and most preferably less than about 0.035 mm. Hydrogel contact lenses suitable for daily wear typically have a water content less than about 55%, preferably less than 45% and/or a center thickness of at least about 0.05 mm, preferably at least about 0.06 mm.

The designation of contact lenses as suitable for daily wear or for extended wear depends on performance and not on its composition or structure. In order to obtain approval by the United States Food and Drug Administration as suitable for extended wear, a lens must be able to be slept in safely. According to an article by Polse and Decker in Invest. Ophthal. Visual Sci., 18, 188 (1979), a contact lens should have an oxygen transmissibility of $5 \times 10^{-9}$ and $15 \times 10^{-9}$ cm$\times$ml $O_2$/sec$\times$ml$\times$mm Hg for open and closed eyes, respectively, in order to provide the necessary oxygen flux of 2 l/cm$^2$ hr to the cornea.

In the present specification and claims, a hydrogel contact lens having a center thickness less than about 0.045 mm, preferably less than about 0.040 mm and most preferably less than about 0.035 mm will be referred to as an "ultrathin" lens. A hydrogel contact lens having a water content of at least about 42%, preferably at least about 45%, and most preferable about 55% will be referred to as a "high water content" lens.

The comfort of a contact lens in an eye depends in part on the exchange of fluid in the area outside the lens with that in the area underneath the lens (i.e. between the lens and eye). Such exchange will be referred to as "tear exchange" in the discussion below.

Hard contact lenses undergo a pumping action due to the pressure exerted by the upper eye lid on the top of the lens, which acts as a fulcrum. This pumping causes the desired exchange of fluid.

Such "pumping", however, does not occur with soft contact lenses; see Mandel, "Contact Lens Practice" 3rd ed, 1981, page 512. Accordingly, there is reduced tear exchange in the eyes of wearers of soft contact lenses. This reduced tear exchange is disadvantageous because it prevents the removal of waste matter and debris from the area underneath the lens. This waste matter and debris, which includes proteins, cells, metabolic products, fragments thereof, and the like, become trapped under the lens. The accumulation of the trapped waste matter and debris contribute to the discomfort of the wearer, and in extreme cases may be harmful to the eye.

At the same time, desirable components of the tear fluid outside the contact lens are prevented from contacting the portion of the eye underneath the lens. Such components may occur naturally in the eye, such as oxygen, or artificially, such as antibiotics or other pharmaceutically active compounds.

Although the efficient pumping action of the hard contact lenses does not occur with soft contact lenses, there is still some movement of a soft contact lens in an eye due to the pressure of the upper eye lid on the lens. This movement permits some tear exchange to occur, but is not always sufficient to prevent the accumulation of waste matter and debris under the lens. Moreover, this desirable movement of the lens in the eye tends to decrease with time as the lens dehydrates, shrinks, and grips the eye more tightly.

Isotonic solutions for improving the comfort of wearing soft contact lenses are known. Such solutions typically contain viscosity enhancing agents, lubricants, surfactants, buffers, preservatives, and salts, and are added directly to a contact lens-containing eye. An example of such a solution is Clerz, manufactured and marketed by Coopervision. The Clerz formula contains, by weight, 0.1% sorbic acid, 0.1% disodium edetate, 0.22% sodium borate, and 1% poloxamer 407, which is a block copolymer of ethylene oxide and propylene oxide.

Shively discloses solutions for use by contact lens wearers who have irregularly structured tear films; see Shively U.S. Pat. No. 4,409,205. Such solutions should be hypotonic; see Shively, "Development of Clinically Acceptable Artificial Tear Formulations" in *Symposium: Ophthalmic Drug Delivery Systems*, Joseph R. Robinson, ed., Am. Pharm. Assoc., publishers, Kansas City, MO, 1980. The solutions of the present invention are, by comparison, isotonic and, therefore, especially beneficial for contact lens wearers having regularly structured tear films.

The known solutions for improving contact lens comfort have not been satisfactory in improving tear exchange. In fact, some of the known solutions prevent such exchange by causing the lens to grip the eye more tightly than the lens would in the absence of the solution. This tighter grip of the eye by the lens decreases the movement of the lens in the eye, and prevents the desired tear exchange.

Accordingly, a need exists for ophthalmic solutions which will loosen the grip of soft, hydrogel contact lenses on the eye and/or will increase the movement of the lens in the eye, permitting an increase in tear exchange.

The principal object of the present invention is to provide ophthalmic solutions which increase the tear exchange in human eyes containing soft, hydrogel contact lenses, contributing to the comfort and safety of wearing such lenses.

In the following description and claims of the present invention, percent is by weight unless otherwise indicated.

SUMMARY OF THE INVENTION

The objects of the present invention have been obtained by providing an ophthalmic solution for improving the exchange of fluid in the area outside a hydrogel contact lens with the fluid in the area underneath the hydrogel contact lens comprising:

(a) 0.0005% by weight to an amount equivalent to 330 milliosmoles/kg of solution of a hydrogel contact lens flattening agent.

It is also extremely advantageous to have the following ingredients present as well:

(b) an amount of a viscosity enhancing agent sufficient to cause the composition to have a Brookfield relative viscosity of 3 to 50 cps; and (c) an amount of an ionic salt sufficient to render the solution substantially isotonic.

The invention also includes a method for improving the exchange of fluid in the area outside a hydrogel contact lens with the fluid in the area underneath the hydrogel contact lens in a human eye comprising adding to said eye an effective amount of such ophthalmic solutions.

DETAILED DESCRIPTION OF THE INVENTION

The gist of the present invention is the discovery that certain compounds cause the base curve of soft, hydrogel contact lenses to flatten significantly. The compounds which cause the flattening of hydrogel contact lenses are known to cause swelling of hydrogels.

This swelling is ordinarily expected to be uniform along the base curve diameter and the sagital height of the contact lens. Such uniform swelling would not flatten the base curve of the lens and would not be expected to significantly cause the lens to move more freely on the cornea of the eye.

It has now been found, however, that some compounds unexpectedly cause swelling preferentially along the base curve diameter of the lens relative to the sagital height. Such preferential swelling causes a temporary flattening of the base curve, inducing a loosening of the grip of the eye by the lens and greater movement of the lens in the eye. This loosening and increased movement, in turn, causes the increased tear exchange. Movement of the lens in the eye double and even greater than double the normal movement may be achieved by means of the present solutions.

The contact lens flattening agent is eventually washed away by the natural fluids of the eye, causing the contact lens to return to its original shape. During the time the base curve is distorted, vision is not normally significantly hampered. Comfort and safety are improved by the flushing of waste matter and debris from underneath the lens. At the same time, desirable components from the eye fluid outside the area under the lens, such as oxygen and pharmaceutically active compounds comes into contact with the area of the eye underneath the lens.

Extended wear contact lenses are maintained in the eye for longer periods of time than are daily wear lenses. Accordingly, the solutions of the present invention are especially useful for wearers of extended wear contact lenses.

Any hydrogel swelling agent which swells a hydrogel preferentially along the base curve diameter preferentially relative to the sagital height and which is suitable for use in a human eye may be used in the present solutions and methods as the contact lens flattening agent. Suitable contact lens flattening agents include, for example, urea, glycerin, propylene glycol, sorbitol, (both 1- and 2-)amino ethanol and mixtures of these agents. The preferred flattening agent is urea.

The concentration of the contact lens flattening agent may be any concentration that will cause the desired effect and still provide an isotonic or substantially isotonic solution. The optimum concentration will depend on various factors, such as the nature of the contact lens and the particular flattening agent used. The concentration will normally be at least 0.0005% by weight, preferably at least 0.005% by weight and most preferably at least 0.01% by weight. In any solution having less than a substantially isotonic amount of the flattening agent, the other ingredients are used, as set forth below, so that the final product is substantially isotonic.

The maximum concentration of the contact lens flattening agent is that amount equivalent to 330, preferably 320, and most preferably 310 milliosmoles/kg.

It has been found that concentrations of contact lens flattening agents greater than about 1% by weight cause a delay in the desired effect until the agent is diluted by the normal functioning of the eye. Accordingly, the maximum concentration is preferably less than 1%, more preferably less than about 0.5% and most preferably less than about 0.3% by weight.

The optimal concentration of the flattening agents useful with the ultrathin and/or high water content lenses as defined above, generally suitable for extended wear is different from the optimal concentration useful with thicker, lower water containing lenses suitable for daily wear.

The optimal concentration of the flattening agent useful with ultrathin and/or high water content lenses is 0.0005 to 0.1%, preferably 0.001 to 0.08%, and most preferably 0.01 to 0.05% by weight.

The optimal concentration of the flattening useful with daily wear contact lenses is 0.1 to 0.3% by weight.

The solutions useful in the present invention are substantially isotonic. Substantially isotonic solutions are defined for present purposes as containing 270–330, preferably 280–320, and most preferably 290–310 milliosmoles/kg of solutes. The tonicity adjusting agent is employed to bring the final solution tonicity within the stated ranges if not already there due to contributions of the other ingredients.

The preferred isotonicity adjusting agents are ionic salts, i.e. alkali metal halides, especially sodium chloride. The solutions of the invention preferably contain an ionic salt in an amount equivalent to at least 0.3% NaCl, preferably at least 0.5% and most preferably at least 0.75%. When determining the concentration of the tonicity adjusting agent, the contribution to tonicity of the contact lens flattening agent and other ingredients present must be taken into account.

The Brookfield relative viscosity of the present invention is preferably adjusted to 3 to 50, preferably 5 to 20, and most preferably 6 to 11 cps by means of a viscosity enhancing agent. Some suitable viscosity enhancing agents include, for example, cellulosic polymers such as hydroxyethyl cellulose, methyl cellulose and carboxymethyl cellulose; polymeric polyalkylene oxides such as polypropylene oxide and polyethylene oxide; polyoxypropylene-polyoxyethylene block copolymers; and polyvinyl alcohol. Viscosities less than 3 cps are possible, but there may be a delay in the flattening effect after the solutions are placed in the eye.

The viscosity enchancing agent should not coat the lens. This is a particular problem with higher molecular weight viscosity enhancing agents. A particularly suitable viscosity enhancing agent is the hydroxyethyl cellulose sold by Union Carbide as QP40, of which a 2% solution has a Brookfield relative viscosity of 80 to 125 cps when measured with a number 1 spindle at 30 revolutions per minute.

The hydrogel contact lenses suitable for use with the present solutions and methods are the usual "soft" contact lenses, which are already well known and which have been popularly accepted by consumers. These lenses are generally made from polymeric hydroxyethyl methacrylate, ethylene glycol dimethacrylate, vinylpyrrolidone, and mixtures thereof. Other hydrogel materials are also known.

Optional ingredients such as preservatives, buffers, surfactants, lubricants, pharmaceutically active compounds and vasoconstricting (i.e. decongesting) agents may also be included in the solutions of this invention.

Preservatives useful in the present invention should not cause irritation to the eye. Strong binding of the preservative to the lens is also undersirable since it causes the preservative to accumulate in the eye. Accordingly, preservatives such as chlorhexidine and those containing quaternary ammonium compounds, such as benzalkonium chloride and mercury-containing organocompounds, such as thimerosal sodium and phenylmercuric acetate are disadvantageous and preferably excluded from the solutions.

Preservatives preferred for use in the present solutions are any effective, non-irritating preservative which is compatible with hydrogels. Some suitable preservatives include sorbic acid and EDTA. The preferred preservative is sorbic acid.

Any biostatic amount of preservative which prevents contamination of the solutions may be used. Some suitable preservative concentrations include 0.001 to 0.5%, preferably 0.1 to 0.25%.

The solutions of the present invention are preferably buffered at pH 6.5 to 8, and preferably at pH 7 to 7.6, more preferably 7.3-7.4, most preferably about 7.3. Some suitable buffers include borate, acetate, citrate, and phosphate buffer systems.

The borate buffers are preferred since it has been unexpectedly found that the contact lens movement promoting agents, and especially urea, are more effective in the presence of the borate buffers. The buffer system is used at a concentration which provides the desired pH. The combined concentration of boric acid and sodium tetraborate decahydrate, the preferred borate buffer components, is, in the completed solution of the invention, typically from 0.3-0.6 weight %.

The surfactants useful in the present invention are non-irritating to the eye and are, preferably, non-ionic. Some suitable examples of surfactants include ethylene oxide-propylene oxide block copolymers such members of the poloxamer series including Poloxamer 407, Poloxamer 338 and Poloxamer 228. Preferred is Poloxamer 407 sold by BASF Wyndotte under the name Pluronic 127.

Other suitable surfactants are polyethylene oxides such as WSRN 10, WSRN 12K and WSRN 60K sold by Union Carbide.

A third suitable surfactant is Toloxapol, which is an oxyethylated tertiary octylphenol formaldehyde polymer.

The amount of the surfactant may be, for example, about 0.01 to 1% and preferably 0.1 to 0.5%.

Some suitable lubricants include, for example, hydroxyethylcellulose, polyvinyl alcohol and polyvinylpyrrollidone.

The lubricants may be present in amounts of 0.01 to 2% and preferably 0.1 to 1%.

The pharmaceutically active compounds useful in the solutions of this invention are those which have a prophylactic or therapeutic effect on eye disorders. Some examples of pharmaceutically active compounds include, for example, pilocarpine hydrochloride for the treatment of glaucoma, phenylephrine for the treatment of red eyes and dexamethasone or flurometholone for inflammatory occular conditions. Various antimicrobial pharmaceuticals for treatment of diseases of mucous membranes may be used, such as clofazimine, pimaricin, neomycin sulfate, chloramphenicol, bacitracin, sulfacetamide, gentamycin, polymixin B sulfate, and the like. The composition is applied to the patient's eye in sufficient amounts to deliver a pharmacologically effective amount.

Suitable vasoconstricting (i.e. decongesting) agents include, for example, 4,5-dihydro-2(1,2,3,4-tetrahydro-1-naphthylenyl)-1H-imidazole, also known as tetrahydrozoline.

The present invention also includes methods for improving the comfort of wearers of hydrogel contact lenses comprising treating the eyes of such wearers with the inventive solutions described above. The administration of the solution to the eyes may be by any suitable method, for example in the form of drops from a standard applicator. Treatments are preferably repeated several times daily, such as 2 to 5 times. The number of drops depends on the concentration of the solution. Typically, 1-5 drops are suitable.

Having generally described the invention, a more complete understanding can be obtained by reference to certain specific examples, which are provided for purposes of illustration only and are not intended to be limiting unless otherwise specified.

EXAMPLE 1

The following solutions are suitable for use in this invention.

| | | | |
|---|---|---|---|
| (a) 0.2% | Boric Acid | } | Borate Buffer pH 7.6 |
| 0.33% | Na tetraborate decahydrate | | |
| 0.2% | EDTA | | |
| 0.1% | Sorbic Acid | | |
| 0.7% | Hydroxyethylcellulose | | |
| 0.2% | Poloxamer 407 | | |
| 1.14% | Urea | | |
| (b) 0.2% | Boric acid | } | Borate Buffer pH 7.6 |
| 0.33% | Na tetraborate decahydrate | | |
| 0.25% | EDTA | | |

-continued

|  |  |  |
|---|---|---|
| 0.15% | Sorbic Acid |  |
| 1.0% | Hydroxyethylcellulose |  |
| 0.8% | Toloxapol |  |
| 0.25% | Urea |  |
| 0.47% | NaCl |  |
| (c) 0.37% | Boric Acid | ⎫ Borate Buffer |
| 0.06% | Na tetraborate decahydrate | ⎭ pH 7.4 |
| 0.2% | EDTA |  |
| 0.1% | Sorbic Acid |  |
| 0.7% | Hydroxyethylcellulose |  |
| 0.76% | glycerol |  |
| (d) 0.2% | Boric acid | ⎫ Borate Buffer |
| 0.33% | Na tetraborate decahydrate | ⎭ pH 7.6 |
| 0.2% | EDTA |  |
| 0.1% | Sorbic Acid |  |
| 0.7% | Hydroxyethylcellulose |  |
| 0.2% | Poloxamer 407 |  |
| 0.001% | Urea |  |
| 0.52% | NaCl |  |
| (e) 0.16% | Boric acid | ⎫ Borate Buffer |
| 0.38% | Na tetraborate decahydrate | ⎭ pH 7.3 |
| 0.2% | Disodium EDTA |  |
| 0.15% | Sorbic Acid |  |
| 0.7% | Hydroxyethylcellulose |  |
| 0.2% | Polyxamer 407 |  |
| 0.03% | Urea |  |
| 0.52% | NaCl |  |
| (f) 0.16% | Boric acid | ⎫ Borate Buffer |

-continued

|  |  |  |
|---|---|---|
| 0.38% | Na tetraborate decahydrate | pH 7.3 |
| 0.2% | Disodium EDTA |  |
| 0.15% | Sorbic Acid |  |
| 0.7% | Hydroxyethylcellulose |  |
| 0.2% | Poloxamer 407 |  |
| 0.02% | Urea |  |
| 0.44% | NaCl |  |

EXAMPLE 2

The flattening of the lens was illustrated in vitro by measuring the base curve diameter (D) with a Nikon Profile Projector Model V-12 and the sagital height (S) with a Jones and Lamson Profile Projector. A lower ratio of S to D implies a flatter lens.

Results:

|  |  | Before Treatment | | | After treatment with aqueous solution of 0.56% urea | | |
|---|---|---|---|---|---|---|---|
| Lens | Run | D (mm) | S (mm) | S/D | D (mm) | S(mm) | S/D |
| AO-SO[1] | 1 | 14.296 | 4.196 | 0.294 | 15.102 | 3.606 | 0.239 |
|  | 2 | 14.059 | 4.127 | 0.294 | 15.051 | 3.633 | 0.241 |
| Hydrocurve II[2] | 1 | 14.325 | 4.083 | 0.285 | 16.404 | 4.013 | 0.245 |
|  | 2 | 14.210 | 4.077 | 0.287 | 17.225 | 4.343 | 0.252 |
| CibaSoft[3] | 1 | 13.755 | 3.578 | 0.260 | 14.182 | 3.660 | 0.258 |
|  | 2 | 14.301 | 3.573 | 0.259 | 14.301 | 3.613 | 0.253 |

(1) The lens is the AO-SO soft contact lens of the American Optical Company, and contains a copolymer of hydroxyethyl methacrylate and polyvinyl pyrrolidone and 55% water.

(2) The lens is the Hydrocurve II soft contact lens of Barns-Hind and contains a copolymer of hydroxyethyl methacrylate and polyvinyl pyrrolidone and 45% water.

(3) The lens is the CibaSoft contact lens of Ciba Vision Care and contains hydroxyethyl methacrylate and 38% water.

EXAMPLE 3

Solutions suitable for use with various lenses.

SPHERICAL DAILY WEAR HYDROGEL LENSES

| TRADE NAME | MANUFACTURER | MATERIAL | % H₂O | THICKNESS (mm) | DIAMETERS | BASE CURVES | POWERS | SOLUTION[1] |
|---|---|---|---|---|---|---|---|---|
| AOSOFT | American Optical | HEMA/NVP/MMA | 42.5 | .12<br>.04 | 13.0<br>13.8 | 7.8 to 9.0 (.3)<br>8.3, 8.6, 8.9 | −10 to +6.50<br>−7.75 to PLANO | D<br>D |
| AQUAFLEX | Coopervision | HEMA/NVP/MMA | 42.5 | .10<br>.05<br>.42 | 13.0<br>13.8<br>13.8 | 7.8 to 9.0 (.3)<br>8.2 to 9.1 (.3)<br>8.3 to 9.4 (.3) | −9.75 to PLANO<br>−20 to +10<br>+10 to +20 | D<br>D<br>D |
| CIBASOFT | Ciba | HEMA | 37.5 | .09<br>.09<br>.03 | 13.8<br>14.5<br>13.8 | 8.3 to 9.2 (.3)<br>8.6, 8.9, 9.2<br>8.3, 8.6, 8.9 | −6 to PLANO<br>−10 to PLANO<br>−6 to −1 | D<br>D<br>D or E |
| C.S.I. | Syntex | GMA/MMA | 38.5 | .05 | 13.8<br>14.8 | 8.0, 8.3, 8.6<br>8.6, 8.9, 9.35 | −20 to +8<br>−20 to PLANO | D<br>D |
| CUSTOM EYES | C.T.L. | HEMA (Tinted) | 38 | .05<br>.06 | 14.0<br>13.5, 14.5 | 8.4, 8.7<br>Spin Cast | −8 to +5<br>−7 to +5 | D<br>D |
| HYDROCURVE | Barnes-Hind | HEMA/Acrylamide | 45 | .07<br>.11<br>.05<br>.05 | 14.5<br>13.5<br>14.5 | Spin Cast<br>8.3, 8.6<br>8.9 | −2 to PLANO<br>−12 to +7<br>−12 to +7 | D<br>D<br>D |
| HYDRON | American Hydron | HEMA | 38 | .05<br>.12<br>.06<br>.04 | 15.5, 16.0<br>13.0<br>14.0<br>13.8 | 9.2 to 10.1 (.3)<br>8.1 to 9.1 (.2)<br>8.4, 8.7, 9.0<br>8.6 | −20 to +20<br>−20 to +8<br>−10 to PLANO<br>−6 to PLANO | D<br>D<br>D<br>D |
| HYDROSIGHT | National Contact Lenses | HEMA/BMA | 43 | .14<br>.06 | 13.5<br>13.8 | 7.8 to 9.2 (.2)<br>8.3, 8.6, 8.9 | −10 to +5<br>−12 to PLANO | D<br>D |
| NATURAL TINT | Bausch & Lomb | HEMA (Tinted) | 38 | 13.5, 14.5 | | | −6 to PLANO | D |
| P.D.C. SAUFLON 70 | P.D.C., Inc. Vision Tech | HEMA MMA/NVP | 38<br>70 | .06 | 14.0<br>14.3 | 8.3 to 8.9 (.2)<br>8.4, 8.7, 9.0 | <br>−8 to PLANO | D<br>E |
| SOFLENS | Bausch & Lomb | HEMA | 38 | | 13.5<br>14.5 | B₃,U₃,O₃,HO₃,L₃,H₃<br>B₄,U₄,O₄,HO₄,L₄,H₄ | −20 to +20<br>−20 to +20 | D or E[2]<br>D or E[2] |
| SOFT COLORS | Ciba | HEMA (Tinted) | 37.5 | .09<br>.09 | 13.8<br>14.5 | 8.3 to 9.2 (.3)<br>8.6, 8.9, 9.2 | −6 to PLANO<br>−10 to PLANO | D<br>D |
| SOFTCON | American Optical | HEMA/PVP | 55 | .10 | 14.0,14.5 | 7.8 to 8.7 (.3) | −8 to +18 | D or E[2] |

TORIC DAILY WEAR HYDROGEL LENSES

| TRADE NAME | MANUFACTURER | MATERIAL | % H₂O | DIAMETERS | BASE CURVES | SPHERES | CYLINDER | AXIS | BALLAST | SOLUTION[1] |
|---|---|---|---|---|---|---|---|---|---|---|
| B & L TORIC | Bausch & Lomb | HEMA/NVP | 45 | 14.0 | 8.3, 8.6 | −6 to +4 | −.75, −1.25, −1.75 | 90° (+20°)<br>180° (±20°) | prism | D |
| HYDROCURVE II | Barnes-Hind | | 45<br>55* | 13.5<br>14.5 | 8.3, 8.6<br>8.8 | −6 to +3<br>−6 to +3 | −1.25, −2.00<br>−1.25, −2.00 | 180° + 25<br>90° ± 25° | prism | E |
| TORIC TORI-SOFT | Ciba | HEMA | 37.5 | 14.5 | 8.6,8.9,9.2 | −6 to +4 | −1, −1.75 | 180° ± 20°<br>90° ± 20° | thin zones | D |

MULTIFOCAL SOFT LENSES

| TRADE NAME | MANUFACTURER | MATERIAL | % H₂O | DIAMETERS | BASE CURVES | POWERS | ADDS | SOLUTION[1] |
|---|---|---|---|---|---|---|---|---|
| AO MULTIVUE | American Optical | HEMA | 38 | 13.8 | 8.3, 8.6, 8.9 | | | D |

-continued

| BI-SOFT | Optical Ciba | HEMA | 38 | 13.8 | 8.3, 8.6, 8.9 | −8 to +8 | +1.50 +3.00 | D |

APHAKIC EXTENDED WEAR

| TRADE NAME | MANUFACTURER | MATERIAL | % H₂O | THICKNESS (mm) | DIAMETERS | BASE CURVES | POWERS | SOLUTION[1] |
|---|---|---|---|---|---|---|---|---|
| C.W. 79 | Bausch & Lomb | MMA/NVP | 79 | | 14.4 | 8.1, 8.4, 8.7 | +10 to +20 | E |

| TRADE NAME | MANUFACTURER | MATERIAL | % H₂O | THICKNESS (mm) | DIAMETERS | BASE CURVES | POWERS | SOLUTION[1] |
|---|---|---|---|---|---|---|---|---|
| HYDROCURVE II | Barnes-Hind | HEMA/Acrylamide | 45 | | 13.5 | 8.3, 8.6, 8.9 | +7 to +20 | E |
| HYDROCURVE II₅₅ | Barnes-Hind | HEMA/Acrylamide | 55 | | 14.0 | 8.5 | +7 to +20 | E |
| | | | | | 14.5 | 8.8 | | E |
| | | | | | 15.5, 16.0 | 9.2 to 10.1 (3) | | E |
| PERMALENS | Cooper Vision | | 71 | | 14.0, 14.5 | 8.0 to 8.9 (.3) | +8 to +20 | E |
| SAUFLON P.W. | Vision Tech | MMA/NVP | 79 | | 14.4 | 8.1, 8.4, 8.7 | PLANO to +20 | E |
| | | | | | 13.7 | 7.5, 7.8 | +20 to +35 | E |
| SOFTCON | American Optical | HEMA/PVP | 55 | | 14.0, 14.5 | 7.8 to 8.7 (.3) | +8 to +18 | D or E[2] |

COSMETIC EXTENDED WEAR

| TRADE NAME | MANUFACTURER | MATERIAL | % H₂O | THICKNESS (mm) | DIAMETERS | BASE CURVES | POWERS | SOLUTION[1] |
|---|---|---|---|---|---|---|---|---|
| B & L 70 | Bausch & Lomb | MMA/NVP | 70 | | 14.3 | 8.4, 8.7, 9.0 | −6 to PLANO | E |
| O₃, O₄ | Bausch & Lomb | HEMA | 38 | | 13.5, 14.0 | Spin Cast | −6 to PLANO | D or E[2] |
| CSI-T | Syntex | GMA | 38 | | 13.8 | 8.3, 8.6 | −7 to PLANO | D |
| | | | | | 14.8 | 8.6, 8.9, 9.3 | −7 to PLANO | D |
| HYDROCURVE II₅₅ | Barnes-Hind | HEMA/Acrylamide | 55 | | 14.0 | 8.5 | −12 to PLANO | D or E[2] |
| HYDROCURVE II TORIC (SEE TORIC SECTION) | | | | | 14.5 | 8.8 | −12 to PLANO | D or E[2] |
| GENESIS IV | Channel | MMA/NVP | 70 | | 14.3 | 8.4, 8.7, 9.0 | −8 to +8 | E |
| HYDROSIGHT 70 | National | MMA/NVP | 70 | | 14.3 | 8.4, 8.7, 9.0 | −8 to +6 | E |
| PDC 70 | P.D.C. | MMA/NVP | 70 | | 14.4 | 8.7, 9.0 | −8 to PLANO | E |
| PERMALENS | Cooper Vision | | 71 | | 13.5, 14.2 | 7.7 to 8.6 (.3) | −20 to PLANO | E |
| | | | | | 14.0 | 7.7 to 8.6 (.3) | PLANO to +8 | E |
| PERMAFLEX | Cooper Vision | HEMA/ | 74 | | 14.4 | 8.7 | −12 to +8 | E |
| SAUFLON 70 | Vision Tech | MMA/NVP | 70 | | 14.3 | 8.4, 8.7, 9.0 | −12 to +8 | E |
| SOFTCON | American Optical | HEMA/PVP | 55 | | 14.0, 14.5 | 7.8 to 8.7 (.3) | −8 to +8 | D or E |

THERAPEUTIC EXTENDED WEAR

| TRADE NAME | MANUFACTURER | MATERIAL | % H₂O | THICKNESS (mm) | DIAMETERS | BASE CURVES | POWERS | SOLUTION[1] |
|---|---|---|---|---|---|---|---|---|
| CSI | Syntex | GMA | 38 | | 14.8 | 8.6, 8.9, 9.35 | −7 to PLANO | D |
| SAUFLON PW | Vision Tech | MMA/NVP | 79 | | 14.4 | 8.1, 8.4, 8.7 | PLANO TO +20 | E |
| SOFLENS | Bausch & Lomb | HEMA | 38 | | 12.5 | U | −9 to PLANO | E |
| | | | | | 13.5 | U₃ | | |
| | | | | | 14.5 | O₄, B₄ | | |
| SOFTCON | American | | 55 | | 14, 14.5 | 7.8 to 8.7 (.3) | −8 to +18 | D or E |

-continued

Optical

*Also approved for extended wear
[1]D represents a solution suitable for a daily wear lens as described in the specification or in example 1(b).
E represents a solution suitable for an extended wear lens as described in the specification or in example 1(d).
[2]Preferred
In the above Table the abbreviations for the materials are:
BMA - butyl methacrylate
GMA - glyceryl methacrylate
HEMA - hydroxyethylmethacrylate
MMA - methylmethacrylate
NVP - N—vinyl pyrrolidone
PVP - polyvinylpyrolidone

What we claim is:

1. An ophthalmic comfort drop solution for intra ocular use with a daily wear hydrogel contact lens so as to improve the exchange of
   (I) ocular fluid trapped between said lens and an eye to which said lens has been applied for
   (II) ocularly compatable fluid not so trapped, said solution consisting essentially of:
   (a) 0.1 to 0.5% by weight of a lens flattening agent selected from urea, glycerin, sorbitol, aminoethanol and mixtures thereof;
   (b) an ocularly acceptable ionic salt in an amount sufficient to give the entire comfort drop solution a tonicity in the range of 270–330 milliosmoles per kilogram of said comfort drop solution;
   (c) an ocularly acceptable viscosity enhancing agent in an amount sufficient to give said comfort drop solution a Brookfield relative viscosity in the range of 3 to 50 cps;
   (d) an ocularly acceptable buffer in an amount of 0% or an effective buffering amount to result in said comfort drop solution having a pH of about 6.5 to about 8;
   (e) 0% to 0.5% of an ocularly acceptable preservative;
   (f) 0% to 2% of an ocularly acceptable lubricant;
   (g) 0% to an ocularly vasoconstricting effective amount of an ocular decongestant;
   (h) 0% to 0.5% of a non-ionic ocularly acceptable surfactant; and
   (i) water.

2. The comfort drop of claim 1 wherein said flattening agent is urea.

3. The comfort drop of claim 1 wherein said flattening agent is present in an amount of 0.1% to 0.4% by weight.

4. The comfort drop of claim 1 wherein said flattening agent is present in an amount of 0.15% to 0.3% by weight.

5. An ophthalmic comfort drop solution for intra ocular use with a daily wear hydrogel contact lens so as to improve the exchange of
   (I) ocular fluid trapped between said lens and an eye to which said lens has been applied for
   (II) ocularly compatable fluid not so trapped, said solution consisting essentially of:
   (a) 0.1 to 0.5% by weight of a lens flattening agent selected from urea, glycerin, sorbitol, aminoethanol and mixtures thereof;
   (b) an ocularly acceptable ionic salt in an amount sufficient to give the entire comfort drop solution a tonicity in the range of 270–330 milliosmoles per kilogram of said comfort drop solution;
   (c) an ocularly acceptable viscosity enhancing agent in an amount sufficient to give said comfort drop solution a Brookfield relative viscosity in the range of 3 to 20 cps;
   (d) an ocularly acceptable buffer in an amount of 0% or an effective buffering amount to result in said comfort drop solution having a pH of about 6.5 to about 8;
   (e) 0% to 0.5% of an ocularly acceptable preservative;
   (f) 0% to 2% of an ocularly acceptable lubricant;
   (g) 0% to an ocularly vasoconstricting effective amount of an ocular decongestant;
   (h) 0% to 1% of a non-ionic ocularly acceptable surfactant; and
   (i) water.

6. The comfort drop of claim 5 wherein said Brookfield relative viscosity is in the range of from 6 to 11 cps.

7. The comfort drop of claim 1 wherein said viscosity enhancing agent is hydroxyethyl cellulose.

8. The comfort drop of claim 1 wherein said ionic salt is present in at least an amount which is equivalent in osmolarity to a solution of 0.3% by weight sodium chloride.

9. The comfort drop of claim 1 wherein said ionic salt is present in at least an amount which is equivalent in osmolarity to a solution of 0.5% by weight sodium chloride.

10. The comfort drop of claim 1 wherein said ionic salt is present in at least an amount which is equivalent in osmolarity to a solution of 0.75% by weight sodium chloride.

11. The comfort drop of claim 1 wherein said ionic salt is sodium chloride.

12. The comfort drop of claim 1 wherein said preservative is ocularly non-irritating.

13. The comfort drop of claim 1 wherein said preservative is present in an amount of from 0.001 to 0.5% by weight of said comfort drop.

14. The comfort drop of claim 1 wherein said preservative is present in an amount of 0.1 to 0.25% by weight of said comfort drop.

15. The comfort drop of claim 1 wherein said preservative is sorbic acid.

16. The comfort drop of claim 1 wherein said pH of said comfort drop is from 7.0 to 7.6.

17. The comfort drop of claim 1 wherein said pH of said comfort drop is about 7.3.

18. The comfort drop of claim 1 wherein said buffer is a borate buffer.

19. The comfort drop of claim 1 consisting essentially of about 0.2% by weight urea; about 0.44% by weight NaCl; about 0.16% by weight Boric Acid; about 0.38% by weight Na tetraborate decahydrate; about 0.2% by weight disodium EDTA; about 0.15% by weight sorbic acid; about 0.7% by weight hydroxyethylcellulose; about 0.2% by weight Poloxamer 407; and water.

20. An ophthalmic comfort drop solution for intra ocular use with an extended wear hydrogel contact lens so as to improve the exchange of
   (I) ocular fluid trapped between said lens and an eye to which said lens has been applied for
   (II) ocularly compatable fluid not so trapped, said solution consisting essentially of:
   (a) 0.0005 to 0.1% by weight of a lens flattening agent selected from urea, glycerin, sorbitol, aminoethanol and mixtures thereof;
   (b) an ocularly acceptable ionic salt in an amount sufficient to give the entire comfort drop solution a tonicity in the range of 270–330 milliosmoles per kilogram of said comfort drop solution;
   (c) an ocularly acceptable viscosity enhancing agent in an amount sufficient to give said comfort drop solution a Brookfield relative viscosity in the range of 3 to 50 cps;
   (d) an ocularly acceptable buffer in an amount of 0% or an effective buffering amount to result in said comfort drop solution having a pH of about 6.5 to about 8;

(e) 0% to 0.5% of an ocularly acceptable preservative;
(f) 0% to 2% of an ocularly acceptable lubricant;
(g) 0% to an ocularly vasoconstricting effective amount of an ocular decongestant;
(h) 0% to 0.5% of a non-ionic ocularly acceptable surfactant; and
(i) water.

21. The comfort drop of claim 1 wherein said flattening agent is urea.

22. The comfort drop of claim 1 wherein said flattening agent is present in an amount of 0.001% to 0.08% by weight.

23. The comfort drop of claim 1 wherein said flattening agent is present in an amount of 0.01% to 0.05% by weight.

24. An ophthalmic comfort drop solution for intra ocular use with an extended wear hydrogel contact lens so as to improve the exchange of
(I) ocular fluid trapped between said lens and an eye to which said lens has been applied for
(II) ocularly compatable fluid not so trapped, said solution consisting essentially of:
(a) 0.0005 to 0.1% by weight of a lens flattening agent selected from urea, glycerin, sorbitol, aminoethanol and mixtures thereof;
(b) an ocularly acceptable ionic salt in an amount sufficient to give the entire comfort drop solution a tonicity in the range of 270–330 milliosmoles per kilogram of said comfort drop solution;
(c) an ocularly acceptable viscosity enhancing agent in an amount sufficient to give said comfort drop solution a Brookfield relative viscosity in the range of 3 to 20 cps;
(d) an ocularly acceptable buffer in an amount of 0% or an effective buffering amount to result in said comfort drop solution having a pH of about 6.5 to about 8;
(e) 0% to 0.5% of an ocularly acceptable preservative;
(f) 0% to 2% of an ocularly acceptable lubricant;
(g) 0% to an ocularly vasoconstricting effective amount of an ocular decongestant;
(h) 0% to 1% of a non-ionic ocularly acceptable surfactant; and
(i) water.

25. The comfort drop of claim 24 wherein said Brookfield relative viscosity is in the range of from 6 to 11 cps.

26. The comfort drop of claim 1 wherein said viscosity enhancing agent is hydroxyethyl cellulose.

27. The comfort drop of claim 1 wherein said ionic salt is present in at least an amount which is equivalent in osmolarity to a solution of 0.3% by weight sodium chloride.

28. The comfort drop of claim 1 wherein said ionic salt is present in at least an amount which is equivalent in osmolarity to a solution of 0.5% by weight sodium chloride.

29. The comfort drop of claim 1 wherein said ionic salt is present in at least an amount which is equivalent in osmolarity to a solution of 0.75% by weight sodium chloride.

30. The comfort drop of claim 1 wherein said ionic salt is sodium chloride.

31. The comfort drop of claim 1 wherein said preservative is ocularly non-irritating.

32. The comfort drop of claim 1 wherein said preservative is present in an amount of from 0.001 to 0.5% by weight of said comfort drop.

33. The comfort drop of claim 1 wherein said preservative is present in an amount of 0.1 to 0.25% by weight of said comfort drop.

34. The comfort drop of claim 1 wherein said preservative is sorbic acid.

35. The comfort drop of claim 1 wherein said pH of said comfort drop is from 7.0 to 7.6.

36. The comfort drop of claim 1 wherein said pH of said comfort drop is about 7.3.

37. The comfort drop of claim 1 wherein said buffer is a borate buffer.

38. The comfort drop of claim 1 consisting essentially of about 0.03% by weight urea; about 0.52% by weight NaCl; about 0.16% by weight Boric Acid; about 0.38% by weight Na tetraborate decahydrate; about 0.2% by weight disodium EDTA; about 0.15% by weight sorbic acid; about 0.7% by weight hydroxyethylcellulose; about 0.2% by weight Poloxamer 407; and water.

39. A method for improving the exchange of
(I) fluid located between a daily wear hydrogel contact lens and an eye to which said lens has been applied, with
(II) an ocularly compatible fluid not so located, while said lens is being worn on said eye comprising instilling to said eye, having said lens thereon, a fluid exchange improving effective amount of a comfort drop solution of claim 1,
whereby said lens is temporarily flattened allowing for greater fluid exchange than is possible in the absence of said comfort drop solution of claim 1.

40. The method of claim 39 wherein said comfort drop is instilled in an amount of 1 to about 5 drops up to about 5 times daily.

41. A method for improving the exchange of
(I) fluid located between a daily wear hydrogel contact lens and an eye to which said lens has been applied, with
(II) an ocularly compatible fluid not so located, while said lens is being worn on said eye comprising instilling to said eye, having said lens thereon, a fluid exchange improving effective amount of a comfort drop solution of claim 19,
whereby said lens is temporarily flattened allowing for greater fluid exchange than is possible in the absence of said comfort drop solution of claim 19.

42. The method of claim 41 wherein said comfort drop is instilled in an amount of 1 to about 5 drops up to about 5 times daily.

43. A method for improving the exchange of
(I) fluid located between an extended wear hydrogel contact lens and an eye to which said lens has been applied, with
(II) an ocularly compatible fluid not so located, while said lens is being worn on said eye comprising instilling to said eye, having said lens thereon, a fluid exchange improving effective amount of a comfort drop solution of claim 20,
whereby said lens is temporarily flattened allowing for greater fluid exchange than is possible in the absence of said comfort drop solution of claim 20.

44. The method of claim 43 wherein said comfort drop is instilled in an amount of 1 to about 5 drops up to about 5 times daily.

45. A method for improving the exchange of (I) fluid located between an extended wear hydrogel contact lens and an eye to which said lens has been applied, with (II) an ocularly compatible fluid not so located, while said lens is being worn on said eye comprising instilling to said eye, having said lens thereon, a fluid exchange improving effective amount of a comfort drop solution of claim 38, whereby said lens is temporarily flattened allowing for greater fluid exchange than is possible in the absence of said comfort drop solution of claim 38.

46. The method of claim 45 wherein said comfort drop is instilled in an amount of 1 to about 5 drops up to about 5 times daily.

* * * * *

UNITED STATES PATENT AND TRADEMARK OFFICE
CERTIFICATE OF CORRECTION

PATENT NO. : 4,748,189
DATED : MAY 31, 1988
INVENTOR(S) : KAI C. SU, ET AL.

It is certified that error appears in the above-identified patent and that said Letters Patent is hereby corrected as shown below:

On the cover page, Item [63], should read
-- Continuation-in-part of Ser. No. 725,065, Apr. 15, 1985, abandoned. --

Signed and Sealed this

Sixteenth Day of July, 1991

Attest:

HARRY F. MANBECK, JR.

*Attesting Officer*     *Commissioner of Patents and Trademarks*